US008552731B2

(12) United States Patent  (10) Patent No.: US 8,552,731 B2
Nichiporov et al. (45) Date of Patent: Oct. 8, 2013

(54) DOSE PROFILE MEASUREMENT SYSTEM FOR CLINICAL PROTON FIELDS

(75) Inventors: Dmitri Nichiporov, Bloomington, IN (US); Keith Solberg, Bloomington, IN (US); Mark Wolanski, Indianapolis, IN (US); Alexander Klyachko, Bloomington, IN (US); Alan Eads, Bloomington, IN (US)

(73) Assignee: Indiana University Research and Technology Corp, Bloomington, IN (US)

( * ) Notice: Subject to any disclaimer, the term of this patent is extended or adjusted under 35 U.S.C. 154(b) by 498 days.

(21) Appl. No.: 12/663,131

(22) PCT Filed: Jun. 5, 2008

(86) PCT No.: PCT/US2008/065857
§ 371 (c)(1),
(2), (4) Date: Dec. 4, 2009

(87) PCT Pub. No.: WO2008/154267
PCT Pub. Date: Dec. 18, 2008

(65) Prior Publication Data
US 2010/0171504 A1    Jul. 8, 2010

Related U.S. Application Data

(60) Provisional application No. 60/989,582, filed on Nov. 21, 2007, provisional application No. 60/942,394, filed on Jun. 6, 2007.

(51) Int. Cl.
*G01N 27/62* (2006.01)
(52) U.S. Cl.
USPC ....................................................... 324/464
(58) Field of Classification Search
USPC .......... 324/459–470; 73/35.08; 250/397, 222, 250/281, 283, 299, 300; 313/424; 315/108, 315/111.91
See application file for complete search history.

(56) References Cited

U.S. PATENT DOCUMENTS

| 4,435,681 | A  | * | 3/1984  | Masuda et al. | 324/459 |
| 4,994,748 | A  | * | 2/1991  | Rasulev et al. | 324/468 |
| 5,422,573 | A  | * | 6/1995  | Bills et al. | 324/460 |
| 6,100,698 | A  | * | 8/2000  | Megerle et al. | 324/464 |
| 6,333,632 | B1 | * | 12/2001 | Yang et al. | 324/464 |
| 6,403,167 | B1 | * | 6/2002  | Lee et al. | 427/525 |

* cited by examiner

OTHER PUBLICATIONS

Torikoshi, Masami et al., "Irradiation System for HIMAC," Journal of Radiation Research, May 19, 2007, vol. 48, Suppl., A15-A25, 2007. (11 pages).*

*Primary Examiner* — Arleen M Vazquez
*Assistant Examiner* — Alesa Allgood
(74) *Attorney, Agent, or Firm* — Keith Swedo; Taft Stettinius & Hollister LLP

(57) ABSTRACT

A beam profile measurement detector is a tool to efficiently verify dose distributions created with active methods of a clinical proton beam delivery. A Multi-Pad Ionization Chamber (MPIC) has 128 ionization chambers arranged in one plane and measure lateral profiles in fields up to 38 cm in diameter. The MPIC pads have a 5 mm pitch for fields up to 20 cm in diameter and a 7 mm pitch for larger fields, providing an accuracy of field size determination of about 0.5 mm. The Multi-Layer Ionization Chamber (MLIC) detector contains 122 small-volume ionization chambers stacked at a 1.82 mm step (water-equivalent) for depth-dose profile measurements. The MLIC detector can measure profiles up to 20 cm in depth, and determine the 80% distal dose fall-off with about 0.1 mm precision. Both detectors can be connected to the same set of electronics modules, which form the detectors' data acquisition system. The detectors operate in proton fields produced with active methods of beam delivery such as uniform scanning and energy stacking. The MPIC and MLIC detectors can be used for dosimetric characterization of clinical proton fields.

16 Claims, 11 Drawing Sheets

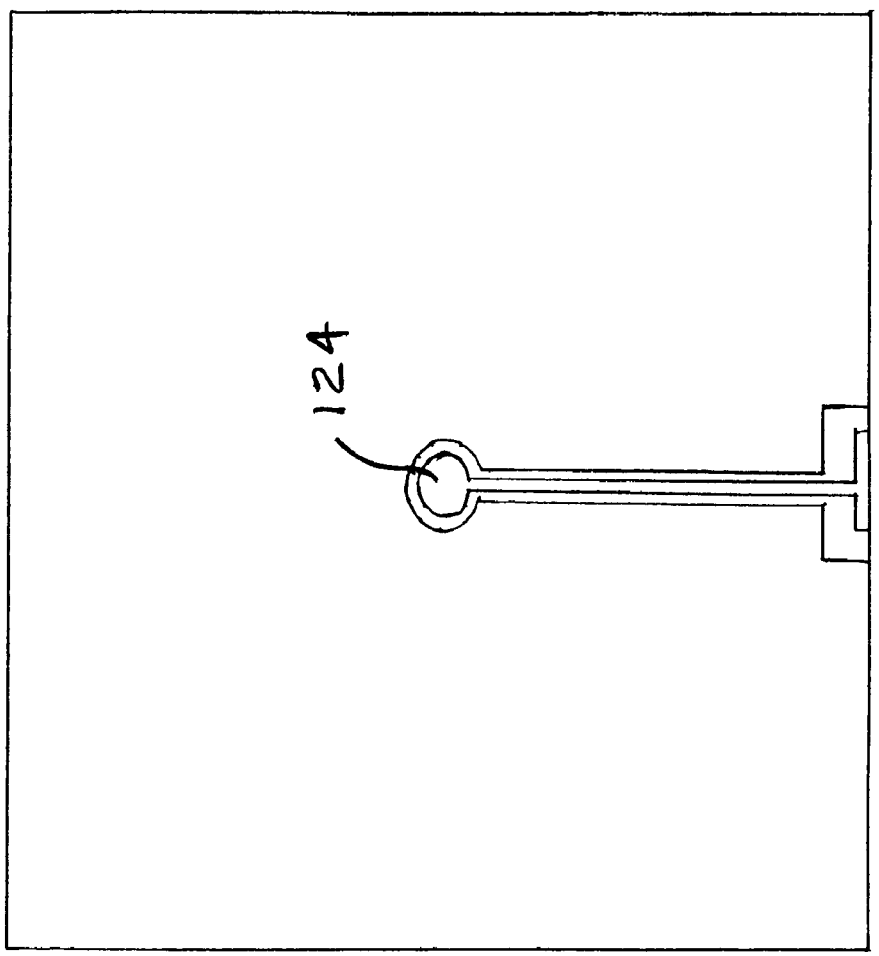

DOSE PROFILE MEASUREMENT SYSTEM FOR CLINICAL PROTON FIELDS

RELATED APPLICATIONS

This application claims the benefit of U.S. Provisional Application 60/942,394 filed Jun. 6, 2007, and of U.S. Provisional Application 60/989,582 filed Nov. 21, 2007, each of which is hereby incorporated by reference herein.

FIELD OF THE INVENTION

The present invention relates generally to beam profile measurement detectors for verifying dose distributions of clinical proton beam delivery.

DESCRIPTION OF THE RELATED ART

Active methods of beam delivery such as beam scanning, and energy stacking are becoming increasingly popular as new clinical proton facilities come in operation. As used herein, "beam scanning" is defined as any method of magnetically deflecting a beam's direction in order to cover a specified area at the treatment room isocenter. Uniform beam scanning is a method of "painting" uniformly a designated area with the beam spot, wherein the beam spot moves along a predefined continuous pattern, and without terminating the beam delivery. The dynamics of dose field production under active methods are different from those used with passive methods such as double scattering and the use of rotating range modulators. While for passive methods the dose rate at any given point in the field is nearly constant in time, this assumption cannot be made for active methods of beam delivery. For example, the method of energy stacking calls for a discontinuous dose delivery as it provides for the layer-by-layer irradiation of the target volume and this process is completed only once for any given field. Instantaneous beam intensity fluctuations due to scanned beam spot and energy stacking pose a new challenge in proton beam measurements because the existing detectors and established measurement techniques are not very well suited for this type of field production scenario.

It should be noted that for proton therapy beams, measurement and verification of depth dose distributions is especially important because protons have a well-defined range of penetration in a material, giving rise to a sharp dose fall-off beyond their penetration depth.

Some of the early attempts to address the problem resulted in detectors such as the Magic Cube and a pixel-segmented ionization chamber, but these instruments had their own limitations. The Magic Cube was designed primarily for experimental studies. In addition to being very bulky, the Magic Cube has the disadvantage of requiring a new setup for each depth measurement. The pixel-segmented ion chamber could not be used for depth dose measurements. Scintillator screens viewed by a charge coupled device (CCD) camera are popular, but these systems are not suited for in-phantom measurements. Integrating detectors such as radiochromic films and alanine detectors can be used, but their use is limited, besides other factors, by the fact that these are not real-time instruments. Some of the earlier devices have matured into commercial products, but none of them can successfully address the whole spectrum of requirements that a detector must meet in order to characterize a dose field created by an actively delivered proton beam.

SUMMARY OF THE INVENTION

The two detectors of the present invention provide lateral and depth dose profile measurements in fields created with methods such as uniform beam scanning and energy stacking. Fields with lateral sizes up to 30 cm in diameter and with Spread-out Bragg Peak (SOBP) modulation up to 15 cm in water may be used. For their characterization, spatial resolution of a few mm laterally and 1 mm or better in depth may be used. However, even the largest commercially available lateral profile detectors do not cover areas bigger than 27 cm×27 cm. No commercial solutions are known that allow the measurement of depth dose distributions in actively delivered proton beams. The detectors' design is based on a static array of detectors that span the entire area of interest—laterally or in depth—and provide information about dose distribution in the process of beam delivery. Both detectors provide a portable measurement system with sufficient precision of measurements while minimizing the number of channels required for the task. The detectors enable the measurement of proton field profiles to which a human patient or other entity will be, or has been, exposed.

The detectors provide significant time savings during measurements in actively delivered beams compared with traditional measurements using a water phantom.

BRIEF DESCRIPTION OF THE DRAWINGS

FIG. 7b is a plan view of the layout of the front side of the high voltage electrode of the MLIC.

DETAILED DESCRIPTION OF THE INVENTION

I. Materials and Methods

Figure 1:
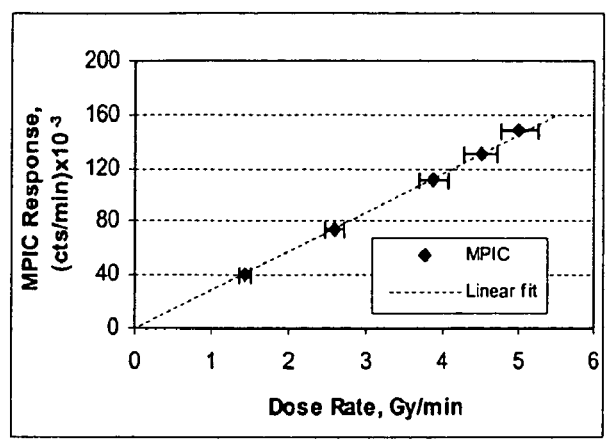
FIG. 1 is a plot of the linearity of the response of the MPIC detector versus dose rate.

For beam commissioning and quality assurance, the two detectors function as a Multi-Pad Ionization Chamber and a Multi-Layer Ionization Chamber. Each detector can be independently positioned at the room isocenter and used for profile measurements, alone, or in combination with water equivalent plastic phantom mounted in front of the detector. Preliminary detector evaluations were conducted in a fixed beam line room with double scattering and range modular wheels. Performance tests were conducted in a room equipped with gantry and active beam delivery technology.

Beam energy (range) was controlled within ±0.1 mm by a beam delivery system that incorporates a double wedge degrader and a multilayer Faraday cup calibrated against the beam range in water. Beam intensity was controlled at the cyclotron such that an intensity of between 1 and 10 nA would be delivered to the gantry nozzle.

Depending on the scanning parameters set for a particular field, the static (unscanned) beam intensity translates into average dose rates of 1.5-5 Gy/min at the gantry room isocenter. These numbers are similar to those found in the fixed beam line room, where typical treatment average dose rates are kept between 0.5 and 1.5 Gy/min, although higher dose rates, up to 6 Gy/min are also available.

A. Detector Design

1. Multi-Pad Ionization Chamber

The Multi-Pad Ionization Chamber (MPIC) is a combination of two orthogonal linear arrays of individual pads laid out on a printed circuit board. This board, which forms the signal plane of the detector, is separated from the high voltage plane by a 3 mm air gap. The detector's sensitive volume is open to atmosphere, which keeps the design simple, and eliminates the need to control temperature and pressure inside the detector. The detector planes are mounted in a housing with the entrance and exit windows made of thin acrylic plates. The windows allow for accurate positioning of the detector at the beam isocenter. The detector's signal plane is located at 4.7 mm water-equivalent depth. The MPIC detector may be installed at the beam isocenter.

In one embodiment, each of the two MPIC arrays is 38 cm long and includes 64 guarded signal pads. Within the 10 cm radius from the detector center, the pads are distributed with a 5 mm pitch, and farther away from the center, with a pitch of 7 mm. This facilitates superior detector spatial resolution for fields of different sizes while keeping the total number of channels at 128, which is a relatively small number.

2. Multi-Layer Ionization Chamber

The Multi-Layer Ionization Chamber (MLIC) is a series of thin polystyrene plates, with a 6 mm diameter signal spot in the center of the plate, interlaced with similar plates, which have a high voltage electrode in the center. A stack of these plates, each measuring 16 cm×16 cm, and separated with 1 mm air gaps, forms the 122-channel MLIC detector. The total water-equivalent depth of the detector is about 220 mm. The detector plates are contained in a housing whose entrance and exit windows are covered with thin acrylic plates. The housing also features two gas ports which allow the MLIC volume to be purged with a gas.

Each plate of the MLIC detector consists of a polystyrene plate 1.5 mm thick, on either side of which a Mylar film is attached. The outer side of the Mylar film has a graphite central spot electrode painted on it; the other side, which subsequently is glued to the polystyrene plate, has a silver paint signal lead painted on it. The lead and the central spot are electrically connected by a plated through via in the Mylar film. This structure is repeated on the other side of the polystyrene plate. Thus, each plate carries two electrodes (high voltage or signal) on its surfaces.

3. Data Acquisition System

In order to save cost and space, the hardware of the data acquisition system may be shared between the MLIC and MPIC. Only one detector can be connected to the data acquisition system at a time.

Outputs of individual detector channels may be connected to the integrator inputs of the data acquisition unit with cables about 10 m long in order to keep the electronics parts away from the radiation area. The data acquisition unit's design is based on eight custom-built modules, each containing a 16-channel gated current integrator module designed under the VME standard. The current from each signal channel is integrated over a user-defined sampling time interval (from 20 microseconds to a few seconds), the collected charge is digitized and sent to the VME bus. A fiber optic link connects the VME bus to the control and data analysis computer located outside of the treatment room.

A remotely controlled dual-channel high voltage power supply provides operating bias voltage for the detectors. The power supply and the current integration modules are mounted on a cart that can be brought into the treatment room before the measurements and removed upon their completion.

Custom software allows the user to control the bias voltage and sampling time interval for either detector. The user can also observe the collection of data in real time and save the information in an ASCII file for off-line analysis. Two modes of data display are available. In dynamic mode, the data collected over each sampling interval are plotted on the screen, allowing the user to observe the profile shape at any moment in time. In cumulative mode, the data collected over the duration of measurement are displayed, providing the information about the dose profile that has accumulated during that duration. The data acquisition in cumulative mode can be terminated and resumed later without the loss of the already collected information. Lateral profiles can be analyzed for field symmetry, flatness and size at the specified isodose level. For depth dose profiles, the range at the specified isodose can be determined. The data interpolation between data points may be based on a simple linear model.

B. Detector Calibration and Performance Tests

Before conducting beam measurements, each current integrator channel in the data acquisition system was tested for linearity in the 0.125-8 nA range using a calibrated current source and was found to be linear within ±2% maximum deviation.

The MPIC and MLIC detectors were evaluated in fields created with 70-200 MeV protons.

For evaluation measurements, each detector was usually placed at the beam isocenter, approximately 5 cm from the final aperture. Most of the measurements were done in cumulative mode, with the sampling period set to 1000 ms and the duration of measurement was typically 1 min.

Field sizes, unless described otherwise, were defined by circular apertures 10 or 20 cm in diameter. Beam energies and delivered doses are quoted for each test as appropriate. All doses and dose rates in this work are quoted for water.

Lateral beam profiles in a water phantom were measured with a small-volume (0.007 $cm^3$) ionization chamber. For depth dose profiles, the Markus chamber (PTW-New York, model TN23343) in a water phantom was used. Under energy stacking, only one point per field delivery could be measured when ion chambers in a water phantom were used.

1. Detector Calibration

Before detector evaluations, the detector channels were calibrated in relative terms to compensate for variations in individual channel sensitivities. The individual channel calibration procedures for the MPIC and MLIC detectors are described later herein.

In order to calibrate the MPIC detector channels, the lateral flatness of a uniform field was verified by measurements using a small-volume ion chamber in a water phantom. Two orthogonal lateral profiles obtained with the ion chamber were fitted with analytical functions (error functions and a polynomial). The MPIC detector was then placed in the same field and exposed to a dose of 1 Gy. The relative calibration coefficients for each channel were derived as the ratio of the fit function to the detector reading for that channel. Because the flat area of the field was only about 27 cm, and was not large enough to cover all detector pads at once, after the first exposure the detector was shifted laterally by 30 mm in each direction (left, right, up, down) from its original position and the exposures repeated. This allowed the completion of calibration of the peripheral pads.

The calibration procedure for the MLIC was performed with the following steps. A depth dose distribution of a 208 MeV proton beam was measured with a Markus ion chamber in a water phantom. The plateau part of the depth profile was fitted analytically with an equation of type $f(R_w) = \alpha^{1/p} \times p \times (1.0 + \beta \times R_w)/R_w^{1/p-1}$, where $R_w$ is the beam range in water, p is the energy-range parameter, $\alpha$ is the effective atomic parameter, and $\beta$ is the proton fluence reduction parameter. The fit function was then scaled to account for the additional fluence reduction due to the beam divergence in the air gaps of the MLIC (inverse square law). The relative calibration coefficient for each MLIC channel was obtained as the ratio of the fit function to the reading in that channel.

After determining the detector calibration coefficients, they were saved in appropriate files and automatically applied to subsequent detector readings.

2. MPIC Detector Performance Tests

The MPIC voltage response curve was measured to determine the detector's optimal operating bias voltage. These tests were conducted in a monoenergetic beam with the nominal energy of 150 MeV at a dose rate of 5 Gy/min. An operating bias voltage of 1500 V was selected for this detector (as described in Sec. III), and this bias was used for all subsequent measurements.

A series of tests were performed to determine the contribution to the MPIC signal from the protons that impinge on the conducting leads. During the tests, the detector was positioned such that proton beams ranging from 2 to 5 cm in diameter were impinging either on the leads, bypassing the signal pads, or on the ground plane, bypassing the leads and the pads. The conducting leads of the MPIC are sized and arranged such that the leads are not susceptible to radiation and do not significantly contribute to the signal carried on the pads. More particularly, the conducting leads are provided with a small size and are disposed on an opposite side of the Kapton film relative the sensitive pads. The conducting leads are electrically connected to the sensitive pads by vias extending through the layer of Kapton, which isolates the conducting lead from the sensitive pad. The leads are also covered with another layer of Kapton film, which is glued onto a support plane (made of G10) for rigidity.

Collection efficiency in the MPIC and its linearity versus dose rate were studied in the dose rate range of approximately 1.5-5 Gy/min, with the detector positioned at the beam isocenter, with no material in front of it.

The dose rate at the isocenter was measured by a patient dose monitor ion chamber located in the gantry nozzle. The beam monitor chamber was calibrated in a reference field and the dose rate measurement precision is estimated at ±5%.

Precision of the MPIC response was evaluated by exposing the detector to a radiation field a number of times, each time delivering a dose of 1 Gy and recording the MPIC response. The lateral profiles were measured in the 150 MeV beam with 10 cm SOBP modulation, at 11 cm water-equivalent depth, which corresponded to the middle of the SOBP plateau.

Finally, in order to evaluate the MPIC performance, the detector was used to measure a lateral profile of a field that had been created with a deliberately distorted flatness, and had 10% nonuniformity ripples in the central area. The field's lateral profile was measured with a small-volume ion chamber in a water phantom using point-by-point measurement technique and also with the MPIC. The 11 cm water-equivalent depth for the MPIC was achieved by placing slabs of Virtual Water™ in front of the detector.

All measurements with the MPIC were performed in air; detector performance with other gases was not studied.

3. MLIC Detector Performance Tests

The MLIC detector's performance was studied in a setup and at beam intensities similar to those used in the MPIC testing. During the measurements, the MLIC detector was purged with dry nitrogen at a flow rate of 0.75 l/min, in order to eliminate the possibility of ambient air humidity affecting the detector plates.

The MLIC voltage response curve was measured in the 0-500V range. Based on the voltage response curve, the operating voltage was chosen to be 200 V.

Contribution to the detector signal from the conducting leads, charge collection efficiency, linearity of signal in dose rate, and reproducibility of the MLIC response were studied. Reproducibility measurements were performed in a 200 MeV beam, which allowed exposing all MLIC channels to approximately equal dose rates of about 1.5 Gy/min.

The MLIC dose rate response was studied in a 150 MeV monochromatic beam. In these tests, the beam intensity was varied at the cyclotron. The beam was stopped in the detector and the dose rate seen by the MLIC channels varied from approximately 0.6 to 5 Gy/min at the entrance to approximately 2 to 18 Gy/min in the channels where the Bragg peak was deposited. The field size for most of the measurements was defined by a circular aperture 10 cm in diameter, except for the trials to study the contribution from the leads, where circular apertures 2 to 4 cm diameter were used.

The MLIC detector was studied at various energies to evaluate the detector's ability to measure beam ranges and SOBP distributions produced with energy stacking. In particular, pristine beams with ranges (at the distal 80%) 16.0, 20.0, and 27.0 cm in water were measured. The same measurements were repeated with the Markus ion chamber in water. For the 27 cm-range beam, a slab of high-impact polystyrene (Boedeker Plastics, Inc., Shiner, Tex.) 8 cm thick was placed in front of the MPIC detector. Additionally, a depth dose profile for a 10 cm SOBP field with maximum energy of 150 McV (16.0 cm range), created with energy stacking, was measured with the MLIC and using the Markus chamber in water. Pristine Bragg peaks in water were measured using a continuous depth scan with subsequent smoothing or employing the point-by-point method. The 10 cm SOBP field in water was measured using the point-by-point technique.

II. Results and Discussion

As stated earlier, the detectors were evaluated both in the fixed beam line room with double scattering and in a room equipped with a gantry and active beam delivery methods. No difference in detectors responses as far as the smoothness of data points or Bragg peak's peak-to-entrance ratio was observed between the two rooms. Therefore, the following discussion does not differentiate between the methods of beam delivery, and the derived conclusions about the detector properties may apply both to passive and active methods of beam delivery.

A. Performance of the MPIC Detector

The tests designed to study extraneous contributions to the detector signal from areas surrounding the signal pads revealed that nowhere in these tests did the extraneous signals from the leads or the ground plane exceed 0.5% of those generated in the signal pads by the same beam. This provides signal-to-noise ratio of about 200, which was regarded as very good for this type of detector and its application.

The MPIC voltage response curve, approached its saturation level in the region of 500 V, exhibiting a nearly constant (±1%) response at higher voltages. However, in order to keep recombination effect at high dose rates to a minimum, the operating bias was set at 1500 V.

MPIC tests performed at different bias voltages were also used to determine ion recombination. Collection efficiency was determined using the classical Bragg-Gray theory applied to the case of a "swept beam" technique using a two-voltage method. At the dose rate of 1.5 Gy/min and at the operating bias voltage, the MPIC collection efficiency was found to be 0.995.

For the MLIC linearity evaluation, readings from the detector's 16 central pads were averaged and the average reading was taken as the detector response. FIG. 1 shows the MPIC response in the 1.5-5 Gy/min dose rate range and a linear fit based on the experimental data. The linear correlation coefficient $R^2$ is 0.999. In the range of dose rates evaluated, the deviation of data points from the fit is less than ±2%.

It can be seen from FIG. 1 that, in the range of beam intensities studied, the MPIC does not exhibit dose rate dependence and that recombination and saturation effects in this range of dose rates are insignificant.

Precision of the MPIC signal was evaluated as a relative standard deviation of channel-by-channel response, calculated for ten identical dose deliveries before applying calibration coefficients. In this case, the field size was about 29 cm in diameter and its uniform area did not cover all the detector pads, leaving a few peripheral pads in the penumbra region of the field. The relative standard deviation and the maximum deviation were computed for each channel. The average standard deviation was 0.4% (1σ), with the average maximum deviation around 1.1%, except for one peripheral channel, which was in the field's penumbra region and where the standard deviation was 2.4%. This includes the stability of the field and of the beam monitor, which we estimate at ±0.1% (maximum deviation).

Figure 2:
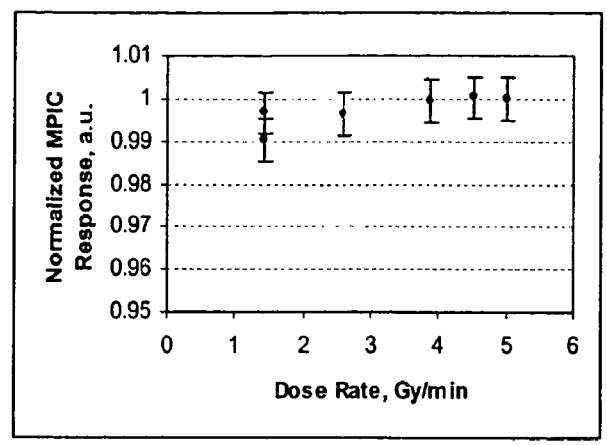
FIG. 2 is a plot of the MPIC response to dose as a function of dose rate.

Relative calibration coefficients for the two arrays of the MPIC detector obtained as described in Sec. I B 1, are shown in FIG. 2. A second calibration repeated a few days later yielded a very similar set of coefficients with root-mean-square (rms) deviation 0.9% (maximum deviation 1.9%, primarily observed in peripheral channels). From the shape of the graphs in FIG. 2 it can be seen that the central pads have smaller area compared with peripheral ones. A slight decrease in coefficients values towards the center suggests that the detector planes are slightly bulging in the vertical direction. A slight asymmetry of the coefficients in the horizontal array also indicates that the signal and bias planes are not exactly parallel. Given the size of the MPIC air gap (3 mm) and the difference in calibration values (about 15%), one can estimate the difference in the air gap size in the horizontal direction at about 0.45 mm.

Figure 3:
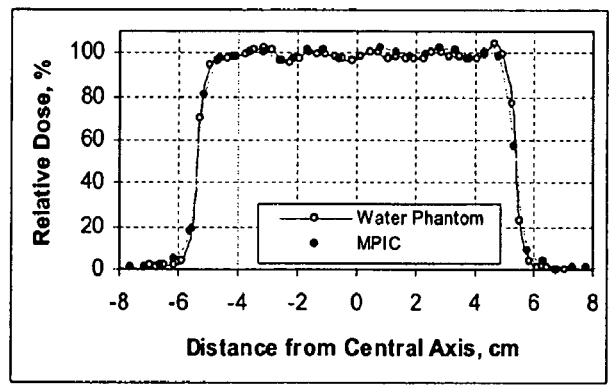
FIG. 3 is a comparison of lateral profiles in a distorted field measured with a small ion chamber in water and with the MPIC detector.

FIG. 3 plots the results of testing the MPIC in the field with the deliberately distorted flatness, with both the MPIC and water phantom profiles being shown. In the range between 100% and 20% of the maximum, the average agreement between the ion chamber and the MPIC detector is very good, about 0.4% (maximum difference 2.8%). The agreement of the 50% isodose measurement is also very good, with no observable difference. Because the linear size of the central MPIC pads (2.5 mm) is close to the internal diameter of the ion chamber (2 mm), the averaging effects in the gradient zones are similar in these detectors. Therefore, the distance to agreement between the profiles measured with these detectors is less than 2 mm at any isodose in the region below 20% of the maximum.

The size of a typical field is defined as the distance between the 50% points on the measured lateral profile. Assuming that the field penumbra covers more than one pad of the detector, and knowing the signal-to-noise ratio for those pads, one can estimate the error in the field size measurement of the detector by approximating the penumbra shape with a Gaussian and computing the first and second moments (centroid and sigma) of the distribution. The accuracy of this calculation depends on the number of pads covered by the field penumbra, which, in our case, typically covered 3 to 5 pads on each side of the profile and the noise was about 0.5% of the signal. For these conditions, the accuracy of field size determination with MPIC was found to be about 0.5 mm. We also found that this accuracy was similar for the central and peripheral areas of the detector, even though the peripheral paid have a larger spacing. This is because large diameter field have larger penumbras which cover more pads. This fact compensates for the inferior spatial resolution in peripheral parts of the MPIC and keeps the accuracy of field size measurement at an acceptable 0.5 mm level.

B. Performance of the MLIC Detector

The MLIC signal pads were chosen to be small in order to allow measurements of depth dose distributions in fields as small as about 2 cm in diameter. However, in the case of a radiation field that is larger than the signal pad, the conducting leads exposed to the proton beam may contribute to the signal from the pad. It was therefore important to study the contribution of the leads to the collected signal. The contribution of the leads was determined by aiming the radiation field at the leads or at the ground planes, thereby bypassing the signal pads. This extraneous contribution was found to be quite small, on the order of 0.25% compared with the signal induced in the signal pads of the MLIC by the same beam.

The MLIC signal pads and high voltage pads may be formed of graphite. The graphite and polystyrene of the MLIC have specific gravities that are close to that of water, and thus, advantageously, the beam properties are close to that of water and of human tissue.

For ion chambers with very small air gaps and for which the mobility of ions is not known with sufficient accuracy, the absolute value of collection efficiency may be determined by a two-point technique using two widely different bias voltages. Because the gap between the MLIC plates is only 1 mm and the detector was purged with nitrogen, this approach was taken in the case of the MLIC. At the dose rate of 5 Gy/min in the Bragg peak region the MLIC collection efficiency was 0.997.

Figure 4:
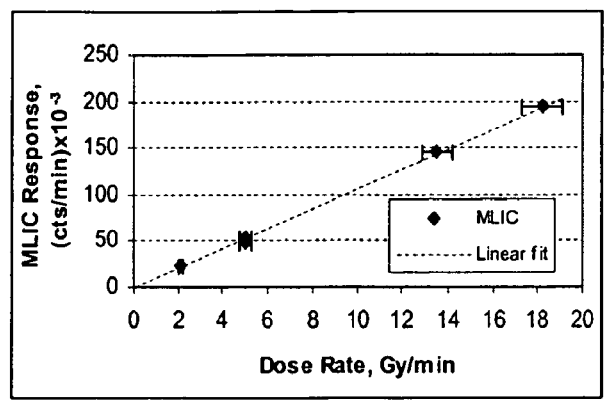
FIG. 4 is a plot of the linearity of the response of the MLIC detector versus dose rate.

Linearity of the MLIC in dose rate evaluated in the range of 2-18 Gy/min is shown in FIG. 4, along with the linear fit to the experimental data. The linear correlation coefficient $R^2$ was 0.999 and the deviation from the linear fit was less than 1.5% for all points except one, where the deviation was around 10%. This is probably due to an error in recording the duration of dose delivery.

Figure 5:
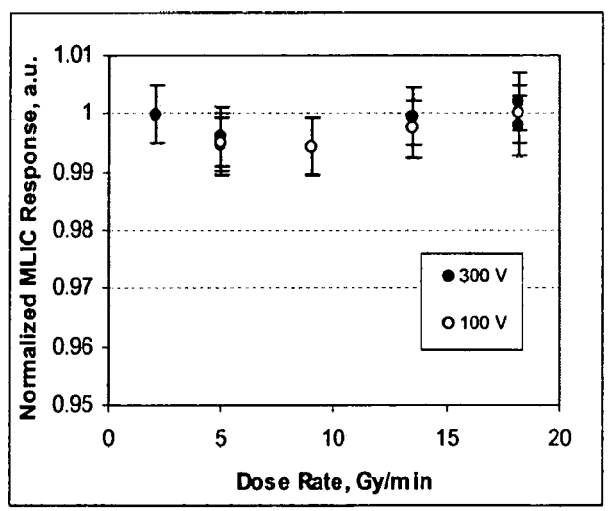
FIG. 5 is a plot of the MLIC response to dose as a function of dose rate at two bias voltages.

Recombination in the MLIC as a function of dose rate, normalized at the maximum dose rate of 18 Gy/min, is shown in FIG. 5 for two voltages, 100 V and 300 V. Across the whole range of dose rates applied, from 5 to 18 Gy/min, at a given voltage, the difference in the MLIC response is less than ±0.5%.

Short-term reproducibility of the MLIC detector response was studied in ten consecutive dose deliveries of 1 Gy and computed for each channel in a way similar to that used in the case of the lateral profile detector. The average standard deviation was 0.2% (1σ), which includes the stability of the beam monitor. The average maximum deviation of the MLIC channels was around 0.4%, except for one channel, where the maximum deviation was 1%.

Calibration procedure for the MLIC is described in Sec. I B 1. The standard deviation of the calibration coefficients across all channels was 14.5%, while the maximum and minimum deviations were −53% and 19%, respectively. These values reproduced very well (within rms) in repeated detector calibrations performed a number of times over a period of one month. The relatively high spread of the calibration coefficients is explained by the difference in the sizes of the air gaps between the plates. Because of the small size of the gap (1 mm), even a 0.1 mm variation introduces a 10% difference in the individual channels' sensitivity. However, the stability of calibration coefficients in time evidenced by the small rms value (±1%) indicates a good long-term stability of the detector calibration.

MLIC resolution in depth is 1.82 mm (water-equivalent) per channel and the beam range at 80% of the distal dose fall-off at a given energy was reproducible to within ±0.1 mm. This value represents the precision of beam range determination, while the absolute value of beam range is dependent on the accuracy of the MLIC calibration against water phantom measurements, which are estimated at ±0.1 mm.

Figure 6A:
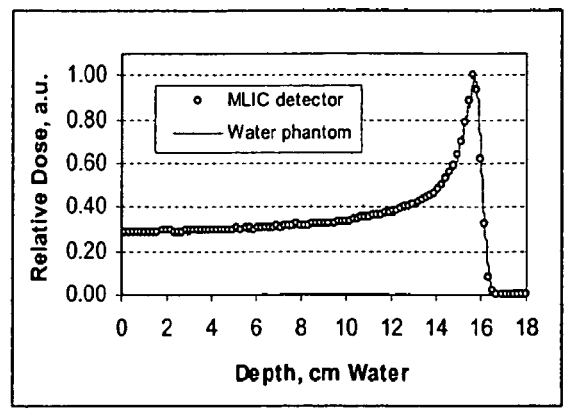
FIG. 6a is a comparison of depth dose profiles measured with a Markus ionization chamber in a water phantom and the MLIC detector. Measurements were performed in a pristine Bragg peak with 16 cm range, normalized at maximum dose.

Depth dose curves for pristine beams with ranges 16.0, 20.0, and 27.0 cm measured with the MLIC and with the Markus ion chamber in water are plotted in FIG. 6(a). For all beam ranges tested, the largest difference between the MLIC range and the range in water, measured at 80% of the distal dose fall-off was less than 1 mm, and typically was on the order of 0.3-0.5 mm. The agreement between the pristine peak profiles in water and the MLIC detector profiles is very good, for most of the points it is better than 1%. Minor disagreements are chiefly due to the fact that the smoothing algorithm (least squares with a sliding window of 31 points) applied to the water phantom profiles obtained with continuous depth scans was not able to completely remove the high fluctuation of signal in the Markus ion chamber caused by the uniformly scanned beam sweeping over the chamber window. The full width at half maximum of the pristine Bragg peaks measured in water and with the MLIC agreed within ±0.1 mm for all peaks measured.

Figure 6B:
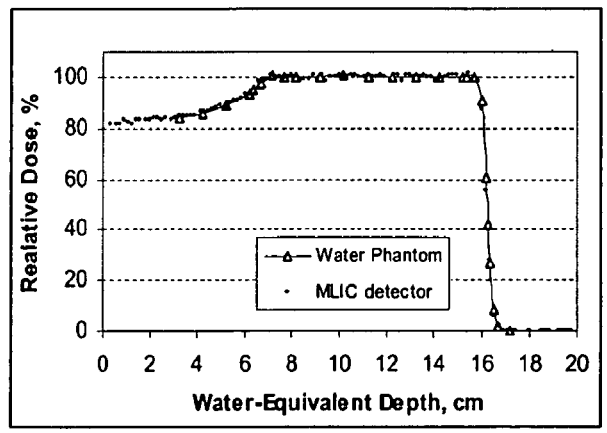
FIG. 6b is a comparison of depth dose profiles measured with a Markus ionization chamber in a water phantom and the MLIC detector. Measurements were performed in a 10 cm SOBP field with 16 cm range, normalized at maximum dose.

MLIC depth dose profiles measured in a field with 10 cm SOBP modulation were compared with the Markus ion chamber measurements in water and are shown in FIG. 6(b).

The agreement between the SOBP profiles measured with the MLIC and ion chamber measurements in water also was very good; the extent of SOBP region at the 90% isodose was 10.5 cm for both detectors. For most of the points, the maximum difference between the MLIC and the water phantom measurements was less than 1% with only a few points showing a difference of 1.5%.

Results of individual channel linearity testing in the data acquisition system using a calibrated current source were applied to the SOBP measurements to determine the absolute calibration of the MLIC. The beam measurements were performed in a 150 MeV beam, with a 10 cm SOBP modulation, shaped with a 10 cm circular aperture. Signals in the four MLIC channels closest to the location of the center of SOBP plateau were averaged and used as the MLIC response. The absolute dose was measured at the center of SOBP with the Markus ion chamber. The MLIC sensitivity was 1.06 nC/Gy.

C. General Remarks

MPIC and MLIC performance tests revealed significant time savings compared with ion chamber point-by-point measurements in a water phantom. A typical exposure of one minute is sufficient to measure two lateral profiles with the MPIC detector, while the point-by-point measurement technique requires the delivery of the full field for each data point measured, and therefore it takes about 100 minutes to collect information for the same number of data points. Besides allowing the use of beam time more efficiently, the detectors provide an additional benefit of reducing the secondary radiation levels in the treatment room.

The dynamic mode of the data acquisition system was useful for quick assessment of a field's quality, while the cumulative mode was employed for quantitative studies. The latter mode can also be used for studies of field superpositions.

The small size of the MLIC pads may be advantageous in studying the effects of Bragg peak degradation as a function of field size.

Performance testing of the MPIC detector revealed its following advantages over existing designs. The MPIC can cover all field sizes (up to 30 cm) available in the gantry room at MPRI; the detector pads are spaced at smaller distances thus providing a better spatial resolution. The MPIC design allows one to use it at any gantry angle, which cannot be achieved with commercial pixel chambers without modifications.

During the MLIC testing it was found that the cables connecting the detector and the integrator modules of the acquisition system may add noise to detector readings. This problem was addressed by allowing the connected cables to sit for a few minutes before taking measurements, which allowed the noise caused by the internal cable friction to subside. Improvements to the data acquisition system are under investigation, with the aim of miniaturizing front-end electronics and providing a better solution to the noise problem.

The current versions of the MPIC and MLIC detectors were intentionally designed as separate instruments in order to allow more flexibility in detector testing and in their use during beam commissioning. However, to better serve specific needs of dosimetric quality assurance activities, it may be useful to fabricate a smaller version of the MPIC detector and incorporate it into the MLIC housing, creating one versatile device for lateral and depth-dose profile verification. This would reduce setup time and allow the simultaneous acquisition of lateral and depth-dose profiles.

III. Conclusions

Two detectors, one for lateral and the other for depth dose measurements, have been designed and tested in proton radiation fields created using passive and active methods of beam delivery. The detectors have been developed as prototype tools for radiation quality assurance measurements in clinical proton beams, to fill a niche of much-needed instruments for beam characterization under uniform beam scanning and energy stacking. The MPIC detector can be used for measurements of lateral beam profiles of up to 30 cm in diameter, while the MLIC facilitates measurements of depth dose profiles of up to 20 cm in depth.

Performance tests of the detectors demonstrated their good precision, spatial resolution, high charge collection efficiency in the dose rate ranges evaluated, and good linearity in dose rate. Both detectors proved to be well-suited for the tasks of beam commissioning at MPRI in clinical proton fields up to 30 cm in diameter created using uniform beam scanning and energy stacking techniques.

Agreement of the MPIC and MLIC profiles with ion chamber measurements in a water phantom was found to be very good, typically better than 1%. This leads to the conclusion that the new detectors can be a successful substitute for water phantom measurements in many dosimetry applications.

Both the MPIC and MLIC detectors facilitate dosimetry measurements, providing significant time savings compared with traditional point-by-point measurements in a water phantom.

IV. MLIC Detector Assembly Description

Figure 7A:
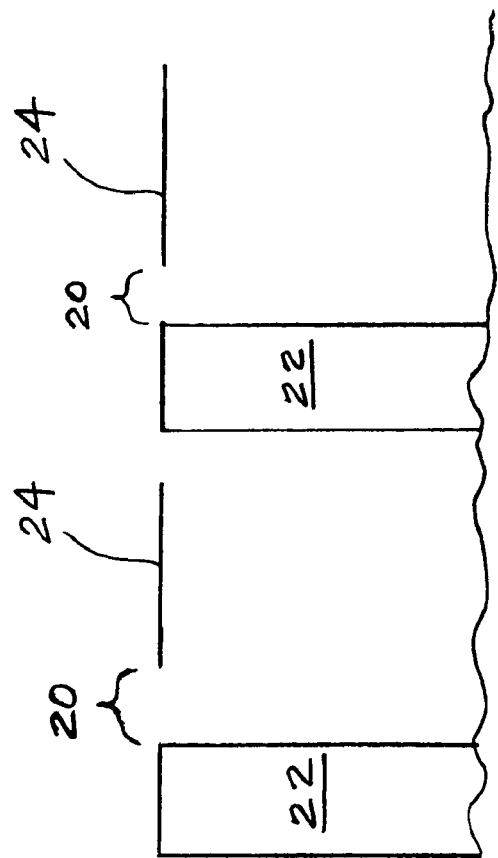
FIG. 7a is a diagram of the order of assembly of the MLIC detector.

The order of the assembly of the MLIC is shown schematically in FIG. 7a. The air gap 20 between the polystyrene with high voltage electrode 22 and the signal pad 24 located on the mylar sheet is 1 mm. The order shown in FIG. 7a is continued until there are 122 signal pads with a high voltage electrode 22 opposite the last signal pad 24.

A "chamber" may be defined herein as the combination of a ground plane, a high voltage electrode and a collection pad. Thus, in the embodiment described above with reference to FIG. 7a, there may be 122 fixed ion chambers aligned in a direction of proton emission. A processor may be in communication with each of the ion chambers in order to determine the level of protons detected by each chamber.

FIG. 7b illustrates one embodiment of the dimensions of the mylar sheet and the configuration of the carbon paint and the silver paint. The circle in the center is the signal, or collection, pad 124. The signal pad is electrically connected by a via to the silver paint on the other side of the mylar sheet. The silver paint acts as a signal lead. Silver paint may provide conductance that is good enough so the charge is accurately measured. The carbon paint is thin and has a low mass. This helps to ensure that the electrodes do not modify the beam too much. Thicker conductors and ones with more mass would interfere with the beam properties. There are other materials that would work for the conductors.

The back side of the mylar, i.e., the side with the silver paint, is covered with a layer of glue. The glue is used to affix the mylar to the polystyrene sheet. The mylar has a nominal thickness of 0.005 inch. The glue layer plus the carbon in layer is measured to be approximately 0.001 inch thick. The polystyrene sheet for both the high voltage electrodes and the collection pads is 0.060 inch thick.

The collection pad is 6 mm in diameter. The carbon paint that surrounds the collection pad acts as a ground plane. The inner diameter of the surrounding ground plane is 8 mm. So there is a 1 mm space between the ground plane and the collection pad.

In the high voltage electrode, the high voltage conductors are fabricated by printing carbon ink onto the polystyrene sheet. The reason for the carbon ink is the same as mentioned above for the signal plane. A circular pad in the center of the polystyrene sheet has a diameter of 10 mm. The high voltage pad is surrounded by a ground plane. The ground plane has an inner diameter of 14 mm. Thus, there is a separation of 2 mm between the high voltage pad and the ground plane. The lead from the edge connection to the high voltage pad is 1 mm wide. The lead and edge connection is also separated from the ground plane by a 2 mm wide space.

The purpose of the ground plane on the signal planes and the high voltage planes is the same as the purpose of the ground planes for the MPIC. The purpose of the ground plane on the polystyrene with the high voltage electrode is to contain any stray electric field lines emanating from the high voltage pads, leads or edge connector. Such stray field lines could cause spurious noise signals if they couple to any lead that connects to the readout for the collection pads. The noise could also be generated by electric field lines coupling to a grounded or ungrounded source near an electrode or signal lead connected to the electronics for the readout pad. Thus, the ground plane helps to shield the readout from noise and spurious signals. The ground plane surrounding the collection pads acts in a similar fashion by capturing electric field lines that could couple to the collection pads or leads from the connection pads to the electronics or any electrode structure found near the collection pads or leads from the collection pads to the electronics.

V. MPIC Detector Assembly Description

Figure 8:
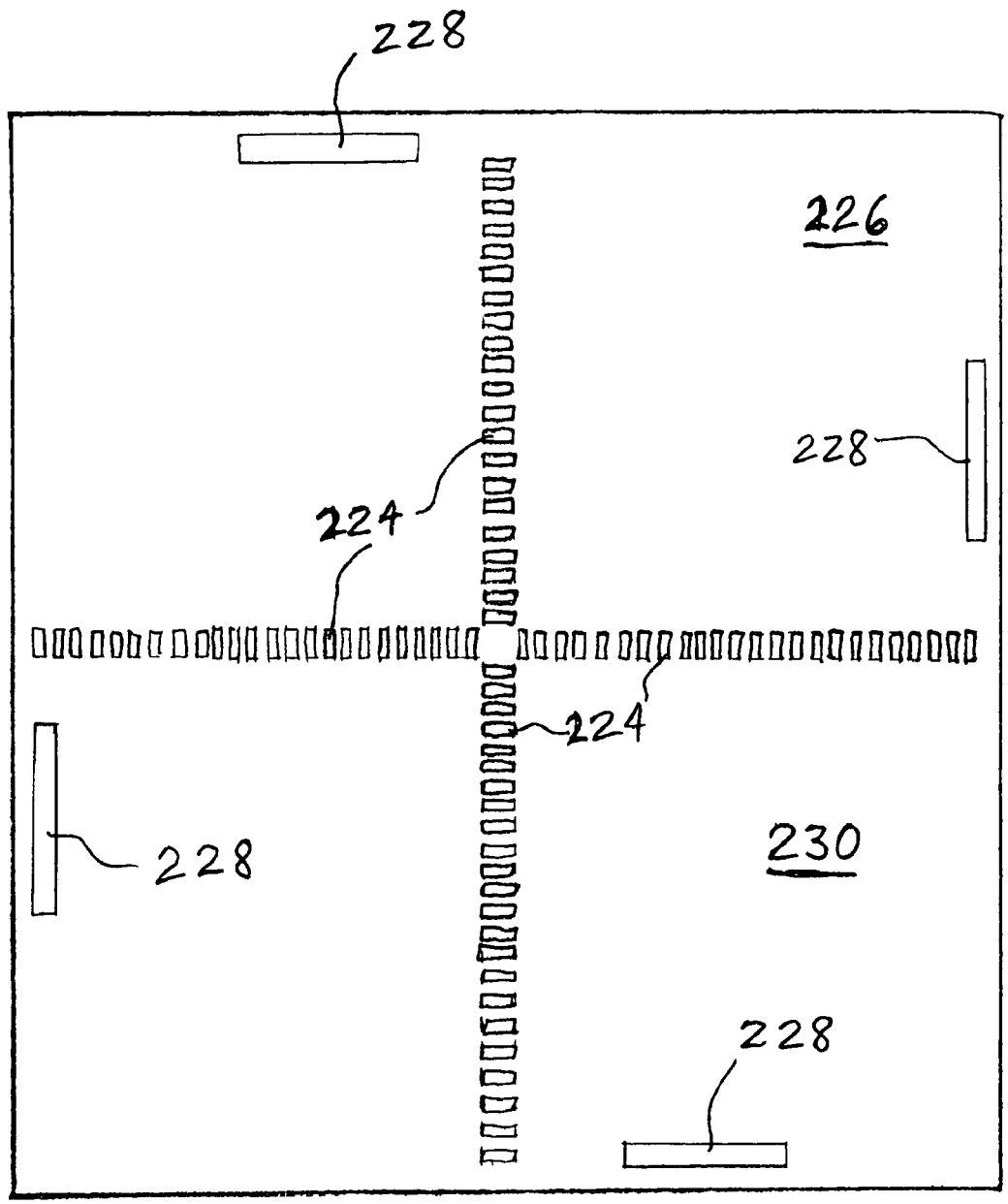
FIG. 8 is a plan view of the top side of a printed circuit board of the MPIC.

The order of the assembly of the MPIC is described herein. The arrangement of signal pads 224 is shown schematically in FIG. 8. FIG. 8 shows collection pads 224 on the top side of a printed circuit board 226. The printed circuit board is a three layer board. Only the top layer is shown in FIG. 8. The collection pads 224 are connected to the edge connectors 228 by signal leads that are buried in the printed circuit board. Connectors 228 may be connected to a microprocessor. The pads are gold plated in order to prevent oxidation and the build up of compounds formed by bounding of chemicals to the surface of the pads. The gold plating is not necessary, but the gold plating may be added in the fabrication process in order to extend the lifetime of the chamber. The remaining area of circuit board 226 in FIG. 8 is a copper ground plane 230. The separation of the signal pads from the ground plane is determined by whatever separation is easily achieved by printed circuit board companies. In one embodiment, the separation is 0.010 inches. But any reasonably small separation may be acceptable. The close proximity of the collection pads and the ground plane is chosen in order to keep the electric field lines that end in the collection pads from coupling to an unwanted voltage source. This voltage source can be the high voltage plane, but could also be an uncovered dielectric that is temporarily charged by the beam or other stray radiation. The spurious source of field lines coupled to the collection pads can cause unwanted noise in the measurements.

Figure 9:
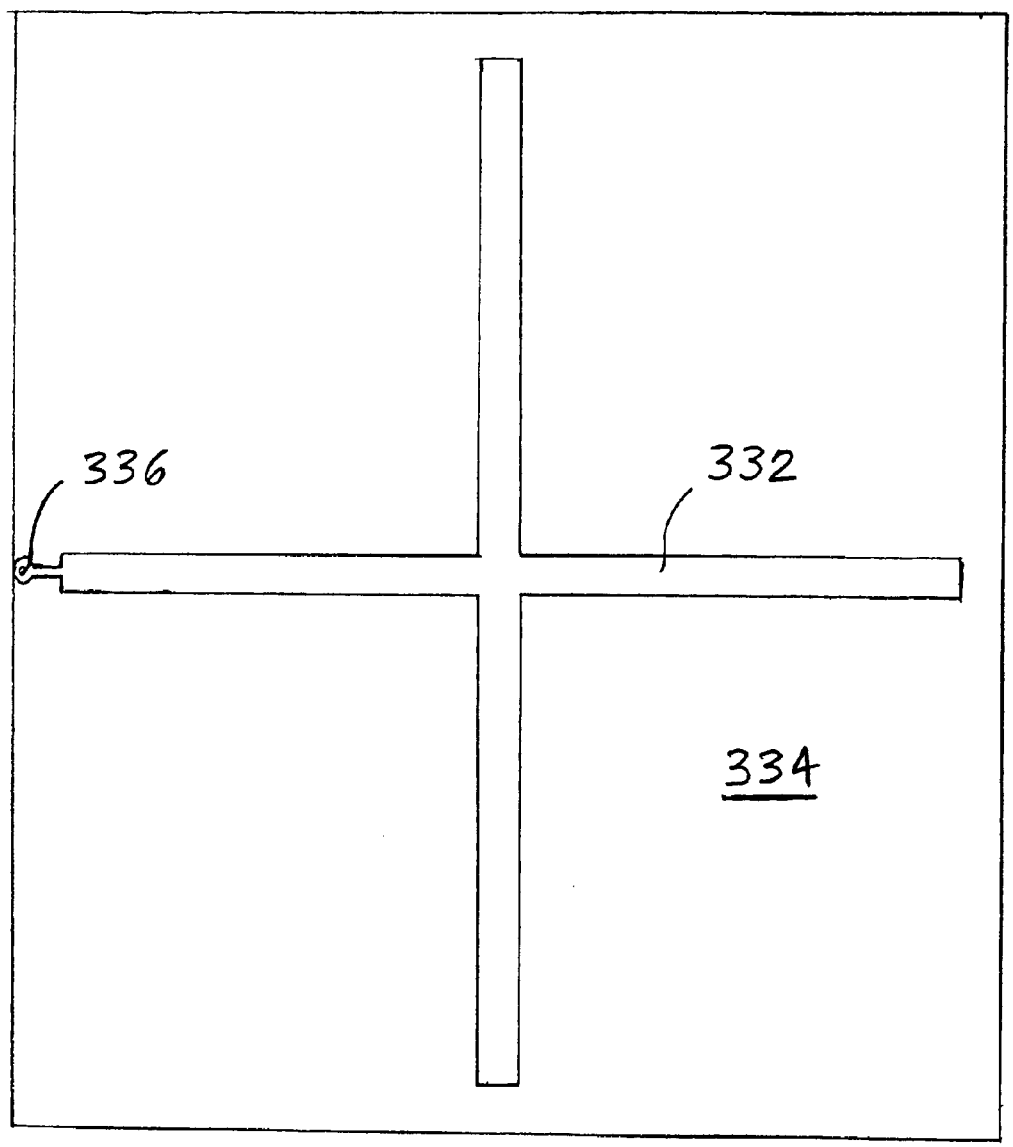
FIG. 9 is a plan view of the high voltage plane of the printed circuit board of the MPIC.
Figure 10:
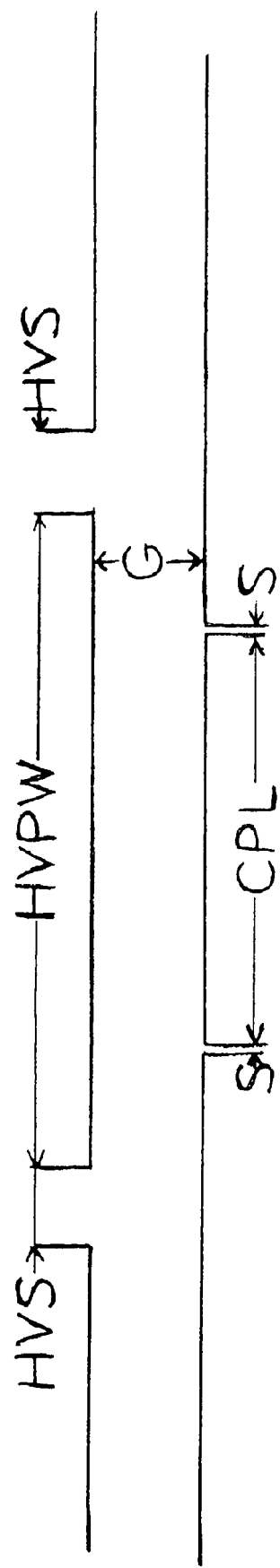
FIG. 10 is a schematic view of the dimensions of the high voltage plane of FIG. 9.

The high voltage plane is shown in FIG. 9, including a cross-shaped high voltage electrode 332, a ground plane 334, and a plated through hole 336 for soldering the high voltage lead. The electrode and electrode-to-collection pad gap dimensions are shown schematically in FIG. 10. In one embodiment of the instrument, the following dimensions were chosen.

G=gap between high voltage pads and collection pads=3 mm
CPL=length of collection pads=10 mm
S=Spacing between collection pads and surrounding ground plane=0.254 mm
HVPW=width of high voltage pads=16 mm
HVS=spacing between high voltage pads and surrounding ground plane=2 mm The purpose of the ground plane on the high voltage printed circuit board is to contain any stray electric field lines emanating from the high voltage pads. Such stray field lines could cause spurious noise signals if they couple to any lead that connects to the readout for the collection pads. The noise could also be generated by electric field lines coupling to a grounded or ungrounded source near an electrode or signal lead connected to the electronics for the readout pad. Thus, the ground plane may help to shield the readout from noise and spurious signals. The ground plane surrounding the collection pads may act in a similar fashion by capturing electric field lines that could couple to the collection pads or leads from the connection pads to the electronics or any electrode structure found near the collection pads or leads from the collection pads to the electronics.

Figure 11D:
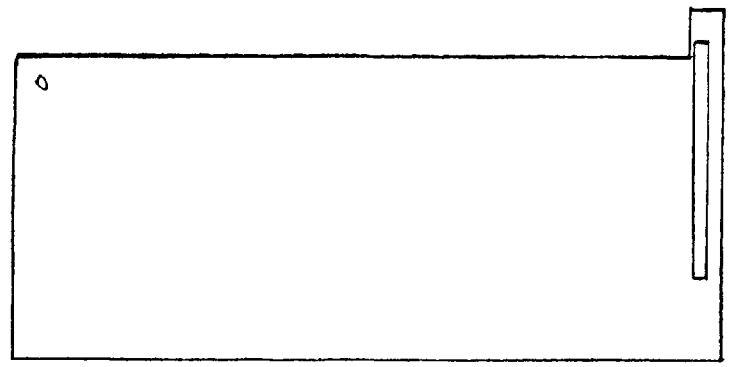
FIG. 11d is a plan view of the bottom layer of the signal collection circuit board of the MPIC.
Figure 11C:
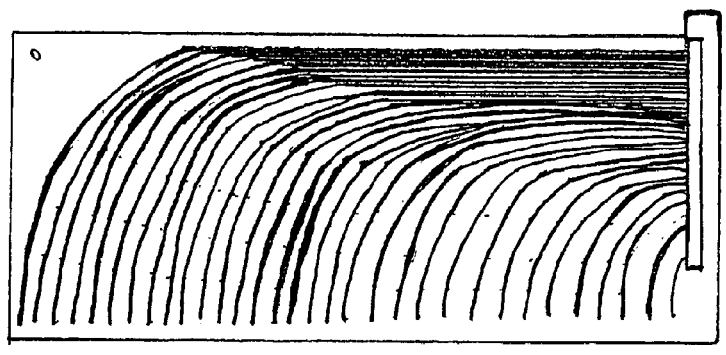
FIG. 11c is a plan view of the middle layer of the signal collection circuit board of the MPIC with the ground plane not shown.
Figure 11B:
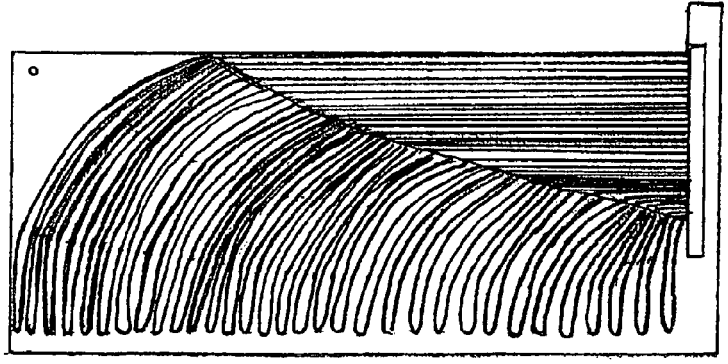
FIG. 11b is a plan view of the middle layer of the signal collection circuit board of the MPIC.
Figure 11A:
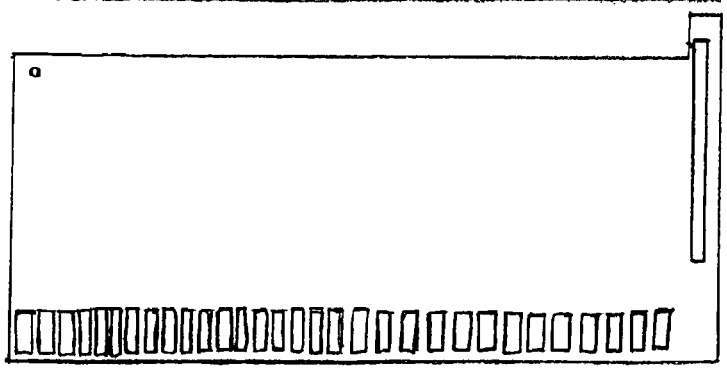
FIG. 11a is a plan view of the top layer of the signal collection circuit board of the MPIC.
Figure 11E:
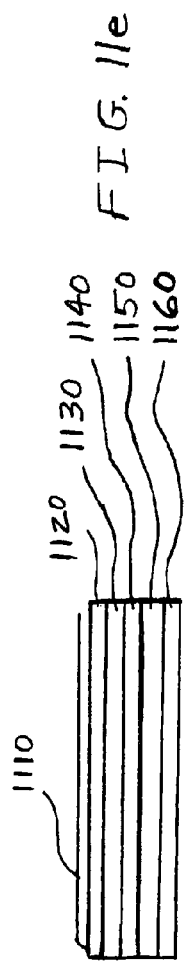
FIG. 11e is a cross sectional view of the signal collection circuit of the MPIC.

In one embodiment of the instrument, the collection electrodes are fabricated with Kapton rather than printed circuit boards. The layout of the Kapton is shown in FIGS. 11a-e. Each kapton circuit may be located with two dowel pin holes and glued to the solid copper clad printed circuit board. FIG. 11a illustrates the top of the signal collection circuit. The rectangles on the left are the collection pads. The area to the right of the collection pads is the copper ground plane. FIG. 11b illustrates the middle layer of the signal collection circuit board. The collection pads are connected to the signal leads by a via. The signal pads are obscured in this view due to the proximity of the signal leads to the ground plane. FIG. 11c illustrates the middle layer of the signal collection circuit board with the copper ground plane not shown. This view clearly shows the signal lead from the via to the card edge connector. FIG. 11d illustrates the bottom layer as seen from the top. The copper ground plane is shown. The card edge connector solder pads are not shown. FIG. 11e is a cross section of the signal collection circuit. This view is not to scale with the other views. A top layer 110 is gold plating. Next is an upper layer 1120 of copper. Next is a layer 1130 of kapton. Next is a middle layer 1140 of copper. Next is another layer 1150 of kapton, and the bottom layer 1160 is kapton.

Figure 12:
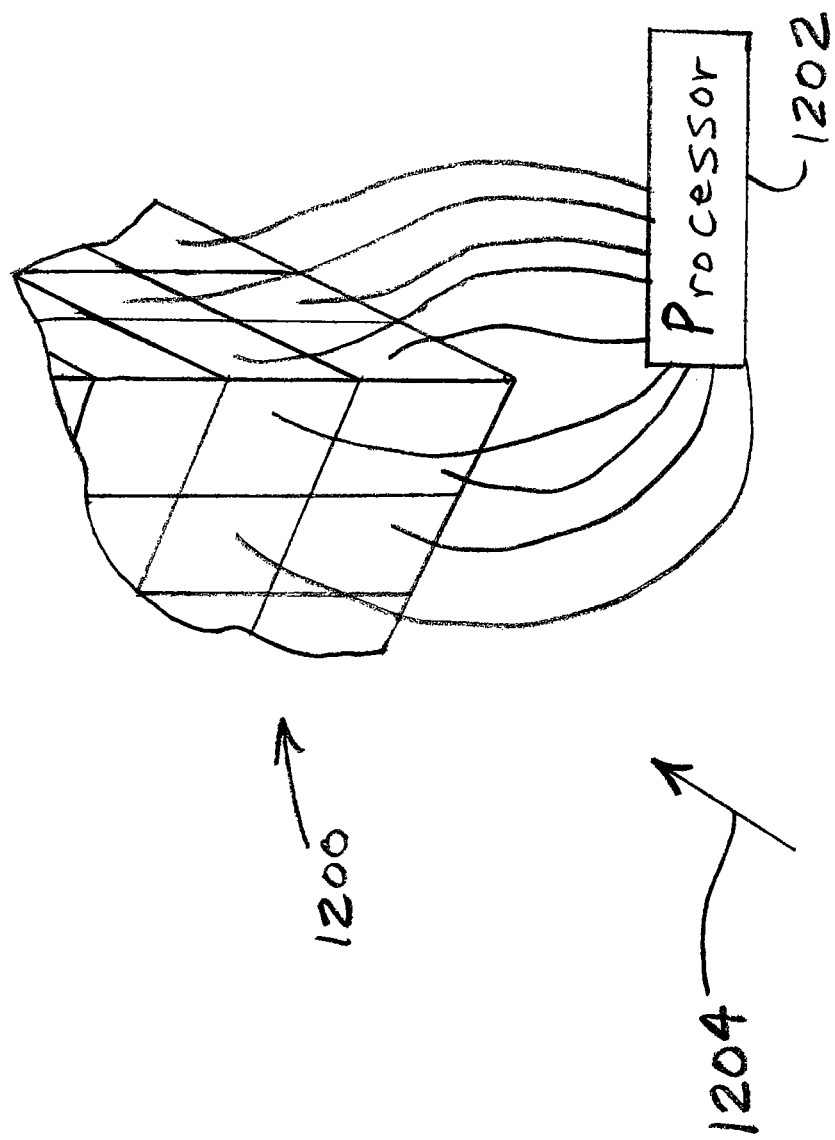
FIG. 12 is a fragmentary schematic diagram of a three-dimensional array of ion chambers.

FIG. 12 is a fragmentary schematic diagram of a three-dimensional array of ion chambers 1200 including a processor 1202 in communication with each of the ion chambers 1200. As shown, some of the ion chambers 1200 are substantially aligned in a direction 1204 of proton emission, and some of the ion chambers 1200 are arranged in a plane substantially perpendicular to direction 1204 of proton emission.

What is claimed is:

1. A proton field measurement apparatus comprising:
   at least one high voltage pad (332);
   a first ground plane (334) surrounding said at least one high voltage pad, said first ground plane and said at least one high voltage pad being coplanar and separated by a first air gap;
   at least one collection pad (224); and
   a second ground plane (230) surrounding said at least one collection pad, said second ground plane and said at least one collection pad being coplanar and separated by a second air gap, said first ground plane and said second ground plane being parallel.

2. The apparatus of claim 1, wherein the high voltage pad and the collection pad are aligned in a direction perpendicular to the first and second ground planes.

3. The apparatus of claim 1, wherein a length of the collection pad is approximately between two and five times larger than a gap between the high voltage pad and the collection pad.

4. The apparatus of claim 1, wherein a width of the high voltage pad is approximately between four and seven times larger than a gap between the high voltage pad and the collection pad.

5. The apparatus of claim 1, wherein a width of the high voltage pad is greater than a length of the collection pad.

6. The apparatus of claim 1, wherein the first air gap is approximately between five and ten times larger than the second air gap.

7. The apparatus of claim 1, wherein a gap between the high voltage pad and the collection pad is greater than both the first air gap and the second air gap.

8. An apparatus for detecting emitted protons, said apparatus comprising:
   a plurality of fixed ion chambers aligned in a direction of proton emission wherein each of said ion chambers comprises a polystyrene plate, each said polystyrene plate having a thickness of less than two millimeters, and wherein the polystyrene plates are parallel; and
   a processor in communication with each of said ion chambers.

9. The apparatus of claim 8, wherein the plates are each separated from adjacent plates by distances of less than 1.5 millimeter.

10. The apparatus of claim 9 wherein each of the plates has a width exceeding 15 cm and a length exceeding 15 cm.

11. An apparatus for detecting emitted protons, said apparatus comprising:
   a plurality of fixed first ion chambers aligned in a direction of proton emission;
   a plurality of second ion chambers arranged in a plane perpendicular to the direction of proton emission; and
   a processor in communication with each of said first and second ion chambers.

12. The apparatus of claim 11, wherein each of said first ion chambers comprises a ground plane (230, 334), a high voltage electrode (332) and a collection pad (224).

13. The apparatus of claim 11, wherein the first ion chambers and the second ion chambers conjunctively form a three-dimensional array of chambers.

14. The apparatus of claim 13, where the first ion chambers comprise one of MPIC chambers and MLIC chambers, the second ion chambers comprising an other of MPIC chambers and MLIC chambers.

15. The apparatus of claim 11, wherein each of said first ion chambers comprises a polystyrene plate.

16. The apparatus of claim 15, wherein each said polystyrene plate has a thickness of less than two millimeters.

* * * * *